US008551407B2

(12) United States Patent
Friedrich et al.

(10) Patent No.: US 8,551,407 B2
(45) Date of Patent: Oct. 8, 2013

(54) BACTERIORHODOPSIN-BASED SENSORS

(75) Inventors: Craig Friedrich, Houghton, MI (US); Donald Lueking, Houghton, MI (US); Mark Griep, Houghton, MI (US)

(73) Assignee: Michigan Technological University, Houghton, MI (US)

( * ) Notice: Subject to any disclaimer, the term of this patent is extended or adjusted under 35 U.S.C. 154(b) by 760 days.

(21) Appl. No.: 12/325,718

(22) Filed: Dec. 1, 2008

(65) Prior Publication Data

US 2009/0142852 A1   Jun. 4, 2009

Related U.S. Application Data

(60) Provisional application No. 60/991,060, filed on Nov. 29, 2007.

(51) Int. Cl.
*G01N 21/01* (2006.01)
(52) U.S. Cl.
USPC .......... 422/82.06; 422/82.05; 422/82.07; 422/82.08; 436/164; 435/7.32
(58) Field of Classification Search
None
See application file for complete search history.

(56) References Cited

U.S. PATENT DOCUMENTS

| | | | |
|---|---|---|---|
| 5,719,033 A | 2/1998 | Ackley et al. | |
| 6,289,717 B1 | 9/2001 | Thundat et al. | |
| 7,303,875 B1 | 12/2007 | Bock et al. | |
| 2005/0093425 A1 | 5/2005 | Sugiyama | |

OTHER PUBLICATIONS

Vangadesh, P. et al., Fabrication and photoresponse of novel carboxymethylcellulose (CMC) based bacteriorhodopsin (bR) sensor, 2006, Organic Electronics, vol. 7, pp. 300-304.*
Chu, Jinfang, et al. Fabrication and photoelectric response of poly(allylamine hydrochloride)/PM thin films by layer-by-layer deposition technique, 2003, Biochemical and Biophysical Research Communications, vol. 305, pp. 116-121.*
Haggie, Peter, Qdots Streptavidin Conjugates from Quantum Dot Corporation, 2005, retrieved from Internet http://www.biocompare. com/Articles/ProductReview/294/Qdots-Streptavidin-Conjugates-From-Quantum-Dot-Corporation.html.*
US 5,834,281, Gremillet et al. (withdrawn).
Griep, M.H. et al., "An integrated bionanosensing method for airborne toxin detection," SPIE Optics & Photonics, Aug. 27, 2007 (20 pages), also published in Proc. SPIE (2007) 6646.
Griep, M.H. et al, "Quantum dots as an onboard light-source for activation of bacteriorhodopsin based nanosensors," 25th Army Sciences Conference, Orlando, Florida (Nov. 2006) 1-6.

(Continued)

*Primary Examiner* — Robert Xu
(74) *Attorney, Agent, or Firm* — Michael Best & Friedrich LLP

(57) ABSTRACT

A sensor comprising a membrane containing bacteriorhodopsin. In one embodiment, the sensor comprises a layer of purple membrane between a first and a second electrode, wherein the electrodes are connected to a circuit such that a signal is produced when a charge is transferred across the membrane. In another embodiment, the sensor comprises a field effect transistor with a layer of purple membrane deposited on the gate. The layer of purple membrane may be further functionalized by adding fluorophores to the layer of purple membrane. The fluorophores may be deposited adjacent to the layer of purple membrane, or the fluorophores may be attached to the layer of purple membrane with linkages. The fluorophores or linkages between the fluorophores and the purple membrane may be functionalized with receptors to produce sensors for targeted chemical or biological species.

11 Claims, 15 Drawing Sheets

(56) References Cited

OTHER PUBLICATIONS

Hampp, N., "Bacteriorhodopsin as a photochromatic retinal protein for optical memories," Chem. Rev. (2000) 100(5):1755-1776.

Hwang, S-B. et al., "Purple membrane vesicles: morphology and proton translocation," J. Membrane Bio. (1977) 33:325-350.

Jovin, T.M., "Quantum dots finally come of age. Two reports demonstrate the specific labeling of cellular constituents with fluorescent quantum dot probes conjugated covalently or electrostatically to antibodies and streptavidin," Nature Biotech. (2003) 21:32-33.

Lakowicz, Principles of Fluorescence Spectroscopy, $2^{nd}$ Edition, Kluwer Academic/Plenumb Publishers, New York (1999).

Medintz, I.L. et al., "Self-assembled nanoscale biosensors based on quantum dot FRET donors," Nature Mat. (2003) 2:630-638.

Wang, W.W. et al., "Photoelectric properties of a detector based on dried bacteriorhodopsin film," Biosensors and Bioelectronics (2006) 21:1309-1319.

\* cited by examiner

FIG. 2
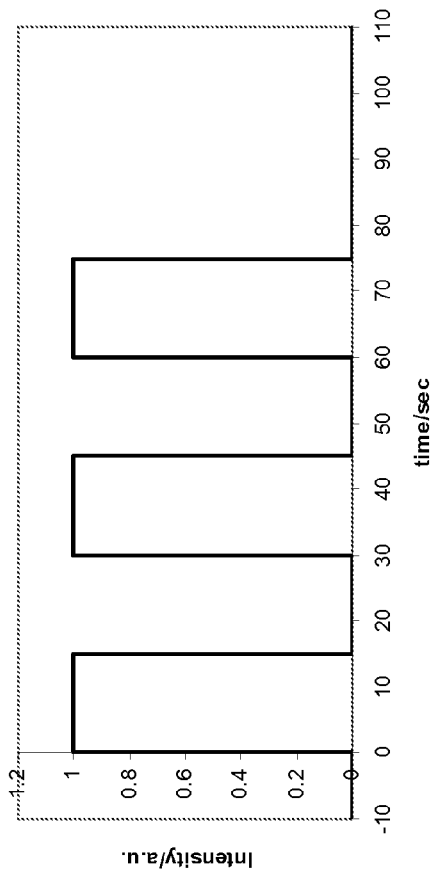
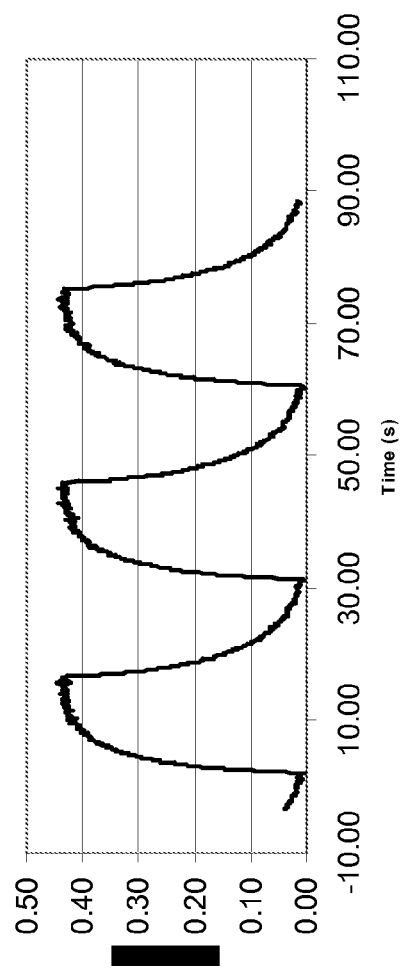

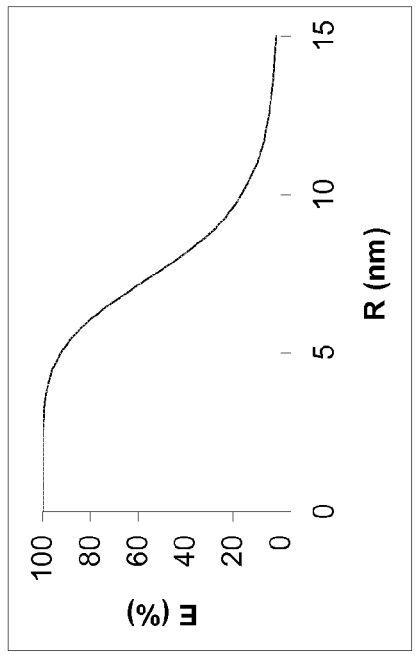
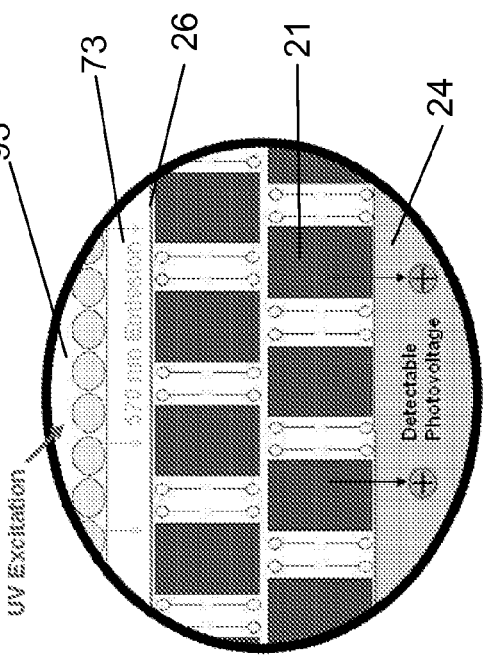
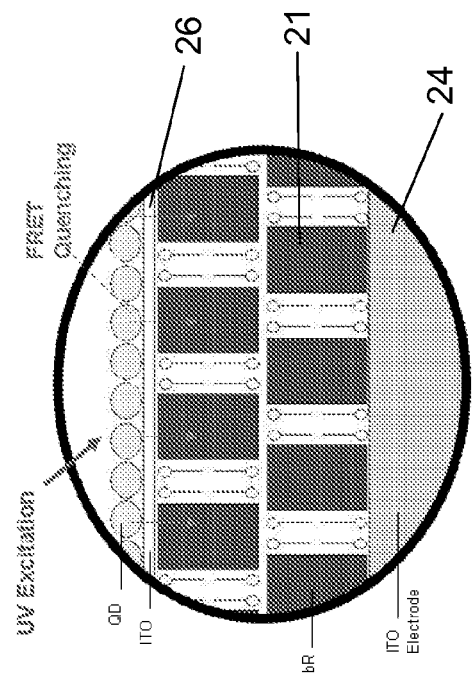

1) Construct Electrode

2) Add biotinylated MBP

3) Add β-CD-QSY9 (Dark Quencher)

4) Introduce Target Molecule (Maltose)

BACTERIORHODOPSIN-BASED SENSORS

RELATED APPLICATIONS

This application claims priority to U.S. Provisional Patent Application Ser. No. 60/991,060, filed Nov. 29, 2007, which is incorporated by reference in its entirety.

STATEMENT REGARDING FEDERALLY FUNDED RESEARCH

This invention was made with U.S. Government support under Grant No. DAAD17-03-C-0125 awarded by the United States Army. The U.S. Government has certain rights in the invention.

BACKGROUND

Bacteriorhodopsin (bR) is a retinal protein that has been intensely studied over the years due to its inherent ability to function as a light-driven proton pump. It is composed of a 248 amino acid peptide with a molecular weight of 26,784 Da and it possesses a covalently attached retinal group. Structurally similar to the visual rhodopsin found in the human eye, bacteriorhodopsin is found in the cell membrane of *Halobacterium salinarium* where it functions to establish a proton and electrochemical gradient for the synthesis of ATP under anaerobic/light conditions. Hampp, *Chem. Rev.*, 100 (5), 1755-76 (2000). Upon illumination with yellow-green light, a proton is pumped from the cytoplasmic side to the extracellular side of the cell membrane. Hwang, *J. Membrane Bio.*, 33, 325-50, (1977). The charge separation resulting from the absorbed light appears 450 fs after the light incidence, implying the potential for a very high frequency sensor. Wang, *Biosensors and Bioelectronics*, 21, 1309-19, (2006).

For engineered applications, bacteriorhodopsin is purified as membrane patches, known as purple membrane (PM). Purple membrane is simply a large cell membrane patch, on average 500 nm in diameter, which is composed of multiple bacteriorhodopsin molecules and their associated lipids. Purple membrane is composed of bacteriorhodopsin and its associated lipids in a two-dimensional crystal. This structure provides it a high degree of chemical stability and resistance to thermal degradation. It is called PM due to its distinct purple color, which is due to its absorption peak near 570 nm.

Purple membrane has many unique properties that make it a viable engineering material. Specifically, PM has been shown to maintain functionality at temperatures up to 80° C. in water and 140° C. dried. Hampp, *Chem. Rev.*, 100 (5), 1755-76 (2000). In the dried state, as well as the wet state, PM retains its light absorption properties and photochemical activity for years.

Quantum dots (QD) are semiconductor particles that have dimensions on the order of a few nanometers or less. When compared to other fluorophores, such as fluorescent dyes, QD's have higher quantum yields, greater chemical stability, longer lifetimes, and a greater resistance to photo bleaching. Jovin, *Nature Biotechnology*, 21, 32-33 (2003). They are also tunable based upon dot diameter. Another important characteristic is that QDs have a broad absorption range coupled with narrow emission spectra. The absorption spectrum for QDs lies primarily in the ultra-violet region while their emission range can be tuned to a very specific wavelength range. Medintz, *Nature Materials*, 2, 630-38, (2003). A QD's emission wavelength is directly dependent upon its diameter, with a diameter of approximately 2 nm yielding photonic emission in the 570 nm range.

SUMMARY OF THE INVENTION

In one embodiment, the invention provides a sensor comprising a membrane layer, containing bacteriorhodopsin, two electrodes, a substrate and a circuit. The membrane layer is arranged between the electrodes, the electrodes being adjacent to the circuit such that the circuit produces a signal when charge is transferred through the membrane between electrodes. When the membrane is exposed to visible light, a charge is transferred through the membrane, thus generating a signal in the circuit. The sensor may achieve additional functionality with the inclusion of fluorophores in proximity to the membrane. The fluorophores can absorb light and then transfer the energy of the light to the bacteriorhodopsin via radiative or non-radiative energy transfer. The fluorophores are optionally quantum dots which may be further functionalized to modify the response of the sensor to particular stimuli, such as targeted chemicals or biological species. A plurality of sensors according to this embodiment may be arranged to produce a chemical or biological sensor with multiple sensitivities.

In another embodiment, the invention provides a sensor comprising a semiconductor transistor having a drain, a source, and a gate, and an adhesion spacer layer adjacent to the gate. A membrane layer, containing bacteriorhodopsin, is adjacent to the adhesion spacer layer. The semiconductor transistor is operatively connected to a circuit such that a change in the gate potential will produce a signal in the circuit. When the membrane is exposed to visible light, the potential at the gate of the transistor changes resulting in a signal in the circuit. The sensor may achieve additional functionality with the attachment of fluorophores to the membrane. The fluorophores can absorb light and then transfer the energy of the light to the bacteriorhodopsin via radiative or non-radiative energy transfer. The fluorophores are optionally quantum dots which may be further functionalized to modify the response of the sensor to particular stimuli, such as targeted chemicals or biological species. A plurality of sensors according to this embodiment may be arranged to produce a chemical or biological sensor with multiple sensitivities.

In another embodiment, the invention provides a sensor comprising a semiconductor transistor having a drain, a source, and a gate, and a membrane layer, containing bacteriorhodopsin, adjacent to the gate. The semiconductor transistor is operatively connected to a circuit such that a change in the gate potential will produce a signal in the circuit. When the membrane is exposed to visible light, the potential at the gate of the transistor changes resulting in a signal in the circuit. The sensor may achieve additional functionality with the attachment of fluorophores to the membrane. The fluorophores can absorb light and then transfer the energy of the light to the bacteriorhodopsin via radiative or non-radiative energy transfer. The fluorophores are optionally quantum dots which may be further functionalized to modify the response of the sensor to particular stimuli, such as targeted chemicals or biological species. A plurality of sensors according to this embodiment may be arranged to produce a chemical or biological sensor with multiple sensitivities.

In another embodiment, the invention provides a method for detecting targeted chemical or biological species in a sample using a bacteriorhodopsin-based sensor according to the invention. The method comprises observing a first signal from a bacteriorhodopsin-based sensor with functionalized fluorophores, in the presence of light with a wavelength shorter than 570 nm, contacting the sensor with a sample, observing a second signal from the sensor, in the presence of light with a wavelength shorter than 570 nm, and comparing the first and second signals. A difference between the first and second signals indicates the presence of a targeted chemical or biological species.

In another embodiment, the invention provides a method for quantifying an amount of targeted chemical or biological species in a sample. A bacteriorhodopsin-based sensor with functionalized fluorophores is exposed to a plurality of calibrated samples of a chemical or biological species, in the presence of light with a wavelength shorter than 570 nm, and the signal from the circuit is recorded for each of the plurality of calibrated solutions. Using known correlation techniques, the signal corresponding to each of the plurality of calibrated samples can be correlated to an amount of targeted chemical or biological species in each of the plurality of calibrated samples. Once the bacteriorhodopsin-based sensor with functionalized fluorophores is calibrated, an amount of a chemical or biological species can be quantified in a sample by correlating the signal from the circuit to an amount of a chemical or biological species.

In another embodiment, the invention provides a sensor array comprising an array of bacteriorhodopsin-based semiconductor transistor sensors. Membrane layers, containing bacteriorhodopsin, are arranged to produce responses in the gates of an array of transistors, the membrane layers may be adjacent to the gates, or the membrane layers may be adjacent to adhesion spacer layers, which are adjacent to the gates. The membranes of the array may be further functionalized by attaching fluorophores to the membranes, thus allowing the fluorophores to radiatively or non-radiatively transfer energy to the membrane when the fluorophores are exposed to light. By adding multiple functionalities to the fluorophores, the array may be made simultaneously sensitive to several targeted chemical or biological species.

Other aspects of the invention will become apparent by consideration of the detailed description and accompanying drawings.

BRIEF DESCRIPTION OF THE DRAWINGS

FIG. 2 is a representation of a sensor response to a blinking LED.

FIG. 12 shows schematic diagrams of wet and dry assemblies and a graph of the efficiency of non-radiant energy transfer as a function of distance.

DETAILED DESCRIPTION OF THE INVENTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The invention provides, among other things, a bacteriorhodopsin-based sensor that can be used to sense light or chemical or biological targets of interest.

Figure 1:
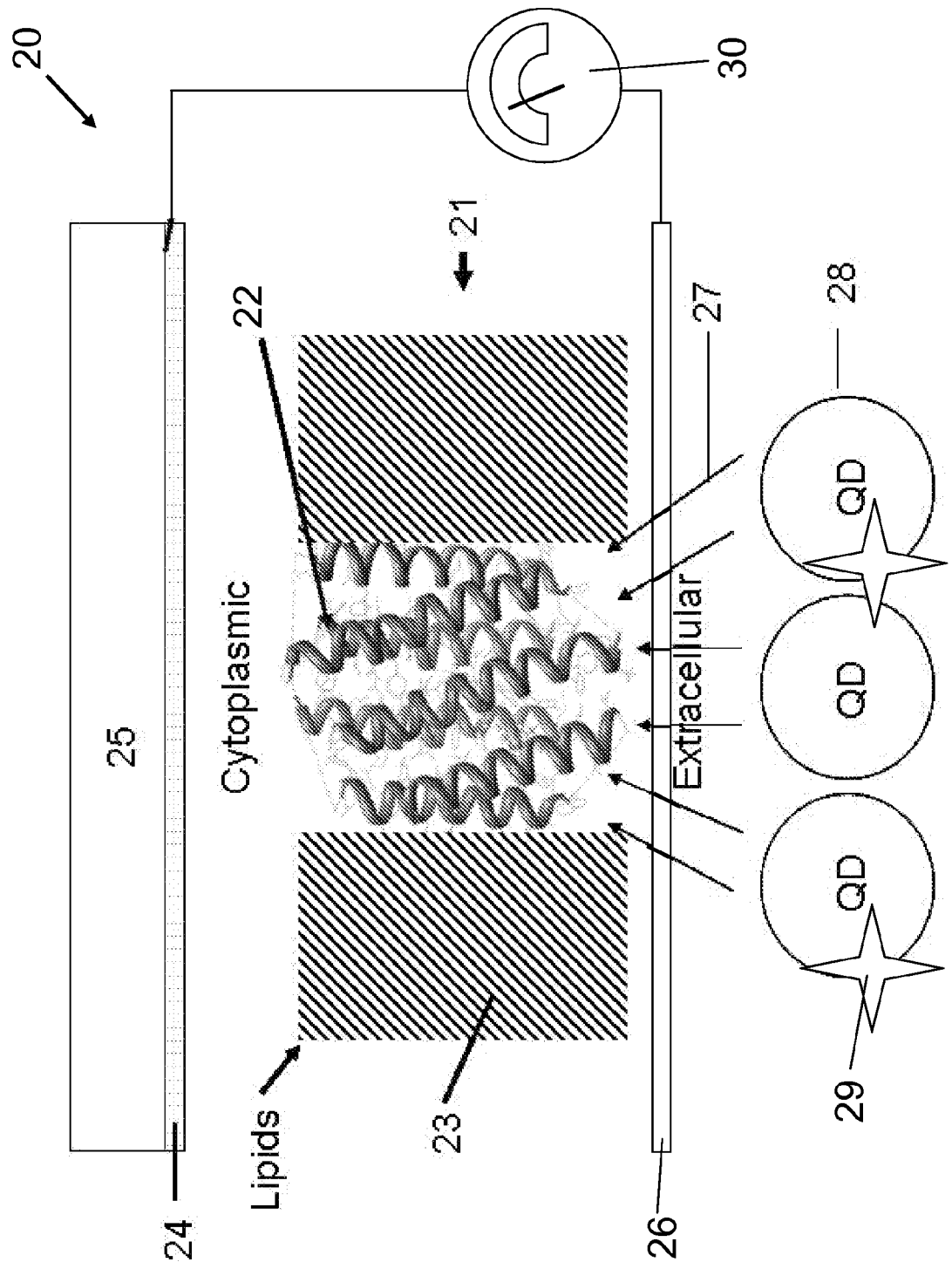
FIG. 1 is a high-level depiction of an embodiment of the invention.

A high level illustration of a bacteriorhodopsin-based sensor 20 is shown in FIG. 1. A layer of purple membrane 21, comprising bacteriorhodopsin 22 and associated lipids 23 is deposited on a first electrode 24 that is adjacent to a substrate 25 which provides structural support for the sensor. A second electrode 26 is placed adjacent to layer of purple membrane 21 opposite first electrode 24. In some embodiments, layer of purple membrane 21 may be nearby or next to second electrode 26 without contacting second electrode 26. In other embodiments layer of purple membrane 21 may contact second electrode 26. First electrode 24 and second electrode 26 may be made by sputtering conductive metals or alloys, such as gold, silver, copper, aluminum, or indium tin oxide, onto a surface, or directly onto layer of purple membrane 21. Other methods of constructing first electrode 24 and second electrode 26 are known to those of skill in the art. For example, electrodes may be a conductive wire (e.g., platinum) used in conjunction with an electrolyte (e.g., potassium chloride). First electrode 24 and second electrode 26 are operatively connected to a circuit 30, such that circuit 30 produces a signal when the charge gradient between first electrode 24 and second electrode 26 changes. As discussed above, when bacteriorhodopsin is exposed to light of approximately 570 nm, a proton is pumped from the cytoplasmic side to the extracellular side of layer of purple membrane 21, resulting in a change in the charge gradient between first electrode 24 and second electrode 26. Accordingly, when bacteriorhodopsin-based sensor 20 is exposed to light of approximately 570 nm, bacteriorhodopsin-based sensor 20 produces a signal.

The response of a bacteriorhodopsin-based sensor 20 is illustrated in FIG. 2. A yellow-green light emitting diode (LED) near bacteriorhodopsin-based sensor 20 is cycled on and off with a 50% duty cycle (upper graph). When the LED is on, bacteriorhodopsin-based sensor 20 develops a charge gradient between first electrode 24 and second electrode 26. The charge gradient results in a measurable signal in circuit 30. The signal increases and then peaks after some time (lower graph). When the LED is off, the charge gradient diminishes through circuit 30, resulting in a falling signal.

Bacteriorhodopsin-based sensor 20 is quite robust, and circuit 30 produces a signal that follows the duty cycle of the LED for hours.

Layer of purple membrane 21 may be "wet" or "dry." "Wet" layer of purple membrane 21 implies that the membrane is in an aqueous environment. Aqueous environments are achieved by building pools or trapped spaces into the sensor. The pools and trapped spaces must be liquid-tight to avoid shorting-out electronic components.

In other embodiments, it is possible to evaporate the liquid from the membrane to produce a "dry" layer of purple membrane 21. Surprisingly, dry membrane layers maintain their charge transfer characteristics, and may be stable for months. Dry membranes allow for easier interfacing to electronic components. However, producing a functional wet bacteriorhodopsin-based sensor 20 is easier than constructing a dry bacteriorhodopsin-based sensor 20 because the membrane layer is more stable in an aqueous environment.

As shown in FIG. 1, bacteriorhodopsin-based sensor 20 may be further functionalized by placing fluorophores 28, in proximity to layer of purple membrane 21. Fluorophores 28 useful for the invention absorb light with wavelengths shorter than 570 nm, typically ultraviolet light, and then transfer some of the energy of the absorbed light to layer of purple membrane 21 via radiative transfer 27 (i.e., fluorescence). Thus, absorption of light by fluorophores 28 and emission within the absorption band of bacteriorhodopsin will result in a change in charge gradient, and ultimately a signal from circuit 30. Sensors employing fluorophores will typically use a shorter wavelength light to activate the sensor, however the response of the sensor to this light is very similar to that shown in FIG. 2.

Figure 3:
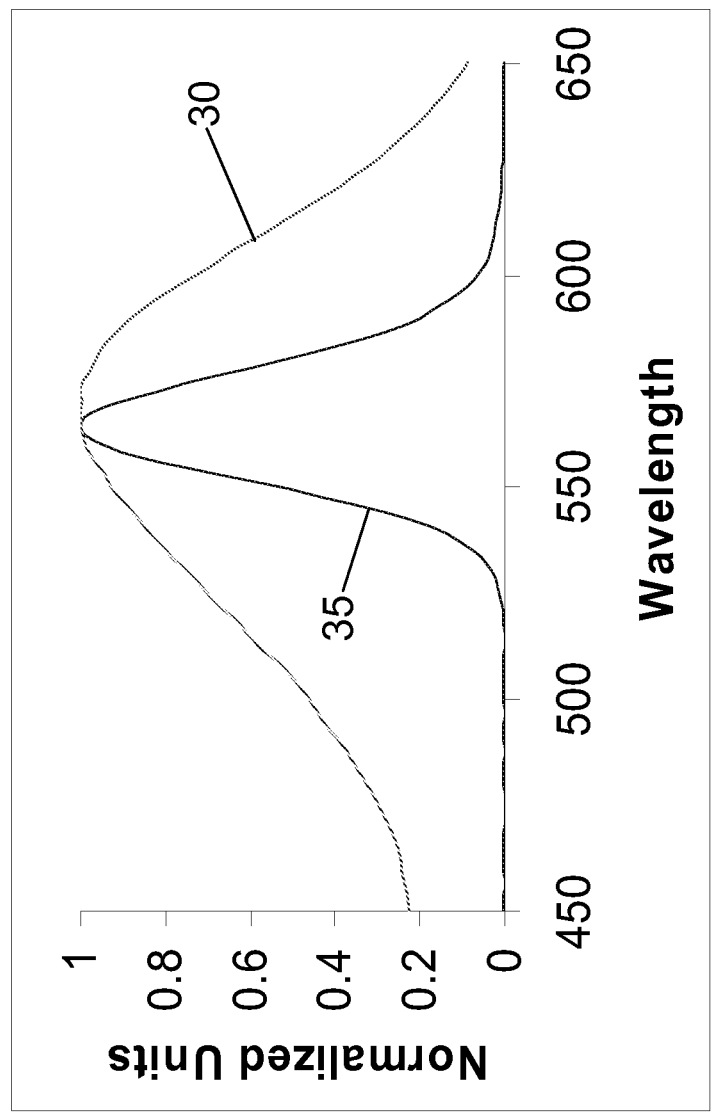
FIG. 3 shows the spectral overlap between a fluorophore emission spectrum and the bacteriorhodopsin absorption spectrum.

Fluorophores suitable for the invention include, but need not be limited to, fluorescent dyes, chromophores, and quantum dots. Fluorophores suitable for the invention typically have an emission spectrum overlapping with the absorption spectrum of bacteriorhodopsin, as shown in FIG. 3. The absorption spectrum of bacteriorhodopsin 30 is rather broad with a peak at approximately 570 nm. In contrast, the emission spectrum of a fluorophore 35 is much narrower. Emission spectrum 35 corresponds to a quantum dot, specifically chosen for its overlapping emission spectrum. The techniques for engineering quantum dots to produce a desired emission spectrum are known to those of ordinary skill in the art.

In some embodiments, the emission spectrum of the fluorophores may be altered by the presence of targeted chemical or biological species. In these embodiments, bacteriorhodopsin-based sensor 20 may become a sensitive chemical or biological sensor. For example, fluorophore 28 in proximity to layer of purple membrane 21 may undergo a conformational change in the presence of a biological species, resulting in an emission spectrum that no longer overlaps with the absorption spectrum of bacteriorhodopsin. Alternatively, for example, the presence of a chemical species may result in a change in the electronic structure of fluorophore 28, thereby shifting the emission spectrum of fluorophore 28 from the peak of the bacteriorhodopsin absorption spectrum. When a binding event causes a shift in the emission spectrum of fluorophore 28, the bacteriorhodopsin will not pump as many protons across the membrane gradient. The decrease in proton pumping diminishes the charge gradient between first electrode 24 and second electrode 26, thus the signal from circuit 30 diminishes. By monitoring for signal drops, it is possible to detect a wide range of binding events with extreme sensitivity.

In embodiments where fluorophores 28 are quantum dots, it is possible to additionally functionalize the quantum dots with receptors 29 that bind targeted chemical or biological species. Targeted biological species may include, but need not be limited to, antibodies, antigens, proteins, nucleic acids, enzymes, and lipids. Targeted chemical species may include, but need not be limited to, antigens, hormones, small molecules, drugs, drug candidates, alkanes, alkenes, alkynes, and aromatic species, as well as substituted alkanes, alkenes, alkynes, and aromatic species. For example, a quantum dot may be functionalized with an antibody. In the presence of light, and in the absence of an antigen that binds that antibody, the quantum dots emit light that overlaps the absorption spectrum of bacteriorhodopsin, producing a signal from circuit 30. When the antibody binds an antigen, however, the emission spectrum of the quantum dot shifts, resulting in a change in the signal of circuit 30. In other embodiments, the emission of fluorophore 28 may be quenched completely, resulting in no signal.

The invention is not limited to the use of antibodies as receptors, however. For example, quantum dots may also be functionalized with the substrate recognition region of an enzyme, or with a binding protein, or with a nucleic acid aptamer. Receptors may be adapted from known biological structures or new receptors may be specifically developed for a sensor of the invention via combinatorial screening or computer-aided design.

Receptors need not be incorporated into, or attached to, the fluorophore, however. The invention also includes receptors incorporated into linker molecules or linkages (discussed below). Such receptors may be sensitive to antibodies, antigens, proteins, nucleic acids, enzymes, lipids, hormones, small molecules, drugs, drug candidates, alkanes, alkenes, alkynes, or aromatic species, as well as substituted alkanes, alkenes, alkynes, or aromatic species Receptors may be additionally incorporated into the bacteriorhodopsin or lipids of the purple membrane using known techniques of genetic engineering and chemical synthesis. In view of this disclosure, one of skill in the art of molecular biology should be able to develop a number of sensors specific to the particular chemical or biological species of interest.

In embodiments where fluorophores 28 are quantum dots, it may be additionally beneficial to use linker molecules to keep fluorophores 28 in proximity to layer of purple membrane 21 so that light emitted from fluorophores 28 is captured by the bacteriorhodopsin in layer of purple membrane 21. Linker molecules may include, but need not be limited to, long-chain organic molecules comprising at least one carbon-carbon double bond. Such long-chain hydrocarbons may include unsaturated fats and/or surfactants. Linker molecules may also comprise oligomers of organic molecules or nucleic acids. In some embodiments, the linker molecules may be streptavidin-biotin constructs. In some embodiments, the linker molecules may be 1-ethyl-3-(3-dimethylaminopropyl) carbodiimide hydrochloride (EDC). Linker molecules additionally may be functionalized with receptors such that the linker molecules will undergo conformational changes resulting in a change in distance between layer of purple membrane 21 and fluorophores 28.

Figure 4:
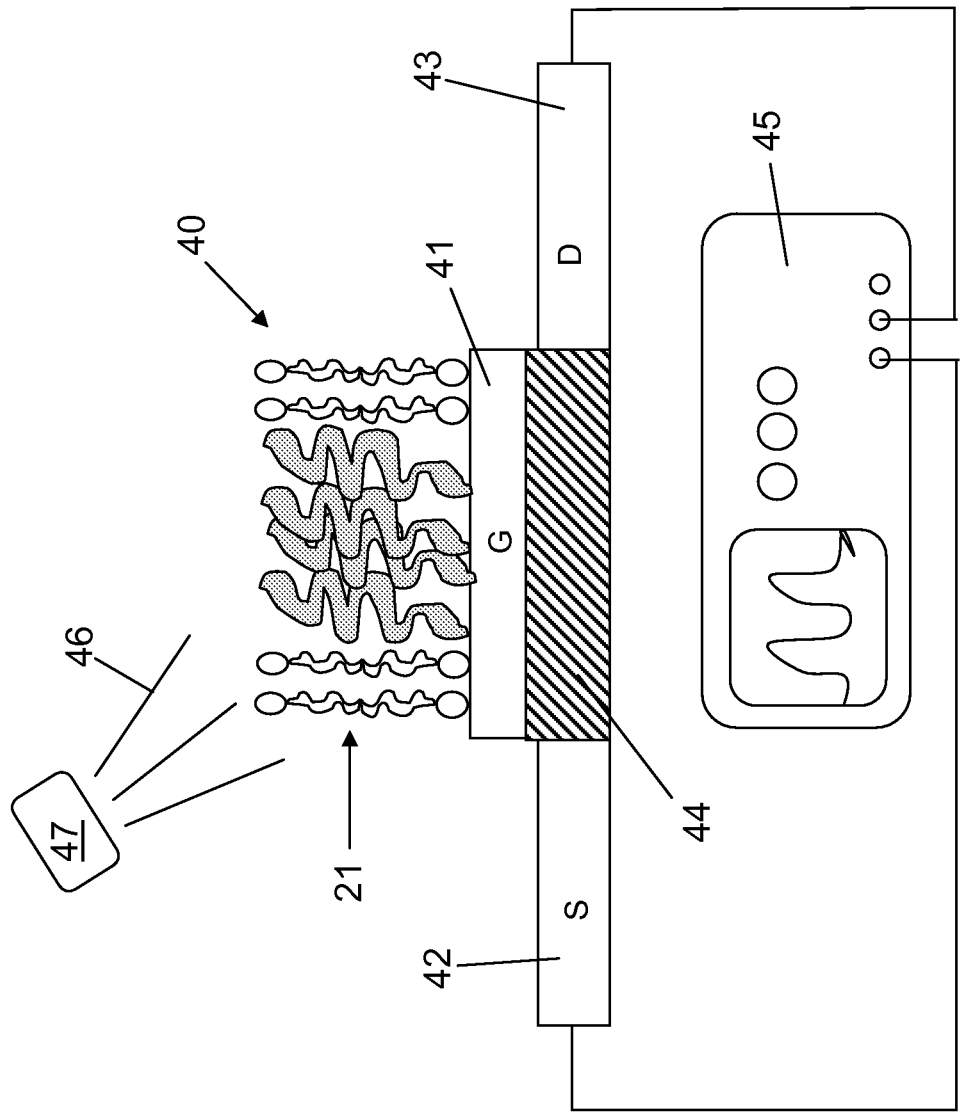
FIG. 4 is a high-level depiction of another embodiment of the invention.

The principles of the invention may be used to produce bacteriorhodopsin-based transistor sensors. A generalized bacteriorhodopsin-based transistor sensor 40 is shown in FIG. 4. Rather than using two electrodes and measuring a change in charge gradient across layer of purple membrane 21, transistor sensor 40 measures variations in the charge density of the cytoplasmic side of layer of purple membrane 21 via a gate 41 of a simple semiconductor field effect transistor (FET).

One embodiment is represented in FIG. 4. The FET is comprised of gate 41, source 42, drain 43, and body 44. Similar to FIG. 1, layer of purple membrane 21 may be directly deposited on the metal surface of gate 41. For transistor sensors 40, layer of purple membrane 21 is typically dried once it is attached to gate 41. The surface area of layer of purple membrane 21 in transistor sensor 40 is typically less than about 10 μm×10 μm, preferably less than about 5 μm×5 μm. The FET is provided with an external power source (not shown). Source 42 and drain 43 are attached to a circuit 45, allowing the potential at gate 41 to be measured as a function of time. Circuit 45 may comprise an oscilloscope, a personal digital assistant, or a personal computer, for example. When transistor sensor 40 is exposed to light 46 from an LED 47, the change in charge density at gate 41 will result in a signal from circuit 45. Modulating the output of LED 47 will result in a modulated signal, as shown in FIG. 2.

FETs suitable for the bacteriorhodopsin-based transistor sensors 40 of the invention may be created using techniques known to those of average skill in the art. Additionally one of skill in the art will be capable of fabricating many FETs on a singular substrate and wiring and powering the FETs individually to create arrays of FETs. One of average skill in the art will also be capable of protecting the subcomponents of the FETs (e.g., with resins) from the solutions used to perform additional processing steps, including the deposition of layers of purple membrane.

In another embodiment, monolayers of purple membrane may be deposited atop the gate of an FET with an exposed metal gate using ionic self-assembled monolayer films. Monolayer deposition may be accomplished by rinsing gate 41 in a strong base to render a net negative charge on the gate, then dipping gate 41 into a solution of poly(dimethyldiallylammonium) chloride to produce a surface of positive charge, and then dipping gate 41 into a solution of purple membrane. Typically, a deposition time of 5 minutes will yield a single monolayer of purple membrane, i.e., bacteriorhodopsin proteins arranged in a singular lipid bi-layer, as depicted in FIG. 4. Typically, a slide strainer is used for the dip steps, however other methods of depositing films are known to those of average skill the relevant art. In this embodiment, the poly(dimethyldiallylammonium) chloride acts as an adhesion spacer layer. Other adhesion spacer layer species may be substituted for poly(dimethyldiallylammonium) chloride.

In other embodiments, monolayers of purple membrane may be deposited without an adhesion spacer layer by directly dipping the gate into a prepared film of purple membrane, e.g., using Langmuir-Blodgett (L-B) techniques. After building up the desired number of monolayers using L-B, it is then possible to functionalize the purple membrane layers with additional L-B films, which may optionally contain fluorophores and/or receptors.

While one monolayer of purple membrane will produce functional sensors, in other embodiments it may be beneficial to deposit multiple monolayers of purple membrane. Multiple monolayers may be achieved through iterative dipping in poly(dimethyldiallylammonium) chloride and purple membrane solutions, or through iterative dipping in an L-B trough without the poly(dimethyldiallylammonium). Bacteriorhodopsin-based transistor sensors 40 of the invention will typically have less than 10 monolayers of purple membrane, or less than 5 monolayers of purple membrane, more typically only 2 or 1 monolayers of purple membrane.

Using alternative adhesion spacer layer species, such as polystyrene sulfonate, it is possible to deposit the extracellular side of layer of purple membrane 21 to gate 41 to produce transistor sensor 40. Attaching the extracellular side of layer of purple membrane 21 to gate 41 will result in a different bias for gate 41. Depending upon the application for transistor sensor 40, a reversed gate 41 bias may be beneficial.

Figure 5:
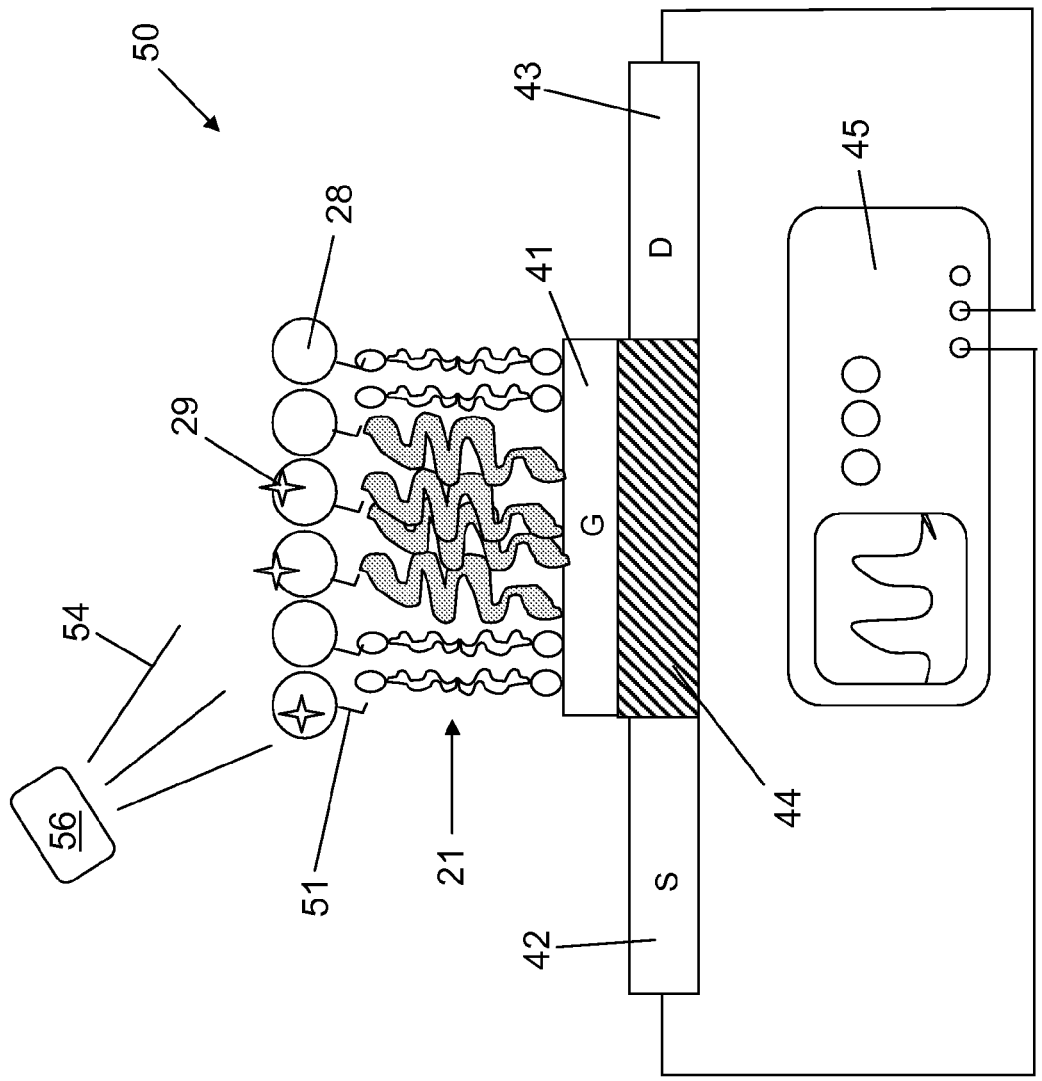
FIG. 5 is a high-level depiction of another embodiment of the invention.

Layer of purple membrane 21 in transistor sensor 40 may be functionalized with fluorophores 28, as shown in FIG. 5 to create a chemical/biological transistor sensor 50. Like transistor sensor 40, chemical/biological transistor sensor 50 comprises layer of purple membrane 21, a FET comprising gate 41, source 42, drain 43, body 44, and circuit 45 for measuring the potential at gate 41. Chemical/biological transistor sensor 50 further comprises fluorophores 28 attached to layer of purple membrane 21. Fluorophores 28 may be attached by depositing additional layers of poly(dimethyldiallylammonium) chloride atop the monolayer(s) of purple membrane, and then dipping the poly(dimethyldiallylammonium) chloride-coated structure in fluorophores 28 having a negative charge. Fluorophores 28 may also be attached with linker molecules such as linkages 51. When chemical/biological transistor sensor 50 is exposed to shorter wavelength light 54, from light source 56, fluorophores 28 will absorb shorter wavelength light 54, and re-emit longer wavelength light (not shown) that coincides with absorption spectrum of bacteriorhodopsin 30, shown in FIG. 3. Shorter wavelengths of light, suitable for activating sensors of the invention, typically comprise light of wavelengths shorter than 570 nm.

Linkages 51 and or adhesion spacer layers are necessary to keep fluorophores 28 in proximity to layer of purple membrane 21 so that light emitted from fluorophores 28 is captured by the bacteriorhodopsin in layer of purple membrane 21. Linkages may include, but need not be limited to, long-chain organic molecules comprising at least one carbon-carbon double bond. Such long-chain hydrocarbons may include unsaturated fats and/or surfactants. Linkages may also comprise oligomers of organic molecules or nucleic acids. In some embodiments, the linkages may comprise streptavidin-biotin constructs. Linkages 51 may also comprise 1-ethyl-3-(3-dimethylaminopropyl) carbodiimide hydrochloride (EDC). Linkages 51 may additionally be functionalized with receptors such that linkages 51 will undergo conformational changes resulting in a change in distance between layer of purple membrane 21 and fluorophores 28.

In some embodiments, linkages 51 may be directly bound to layer of purple membrane 21. Direct binding is possible by using streptavidin-biotin constructs, for example. First, bacteriorhodopsin is biotinylated by mixing biotin into a suspension of purple membrane fragments in 0.1 M sodium bicarbonate buffer (pH of about 8.5). During mixing, the biotin attaches to lysine residue 129 in the bacteriorhodopsin protein. Next, the purple membrane fragments can be reassembled into layer of purple membrane 21 by using membrane assembly techniques, including, but not limited to, electrophoretic sedimentation. Then fluorophore 28 is functionalized with streptavidin using techniques known to those of average skill in the art. Finally, when streptavidin-functionalized fluorophores 28 are deposited onto layer of purple membrane 21, the streptavidin binds to the biotin functionalized bacteriorhodopsin, resulting in linkage 51 between layer of purple membrane 21 and fluorophore 28.

In addition to keeping fluorophores 28 bound to layer of purple membrane 21, it is preferably that linkages 51 maintain a specific distance between fluorophores 28 and the bacteriorhodopsin in layer of purple membrane 21 to maximize the signal produced as a result of a change in distance between fluorophore 28 and layer of purple membrane 21. As has been well-described (Lakowicz, *Principles of Fluorescence Spectroscopy* (1999)) the efficiency of non-radiative energy transfer (Förster energy transfer) is a function of the distance between fluorophore 28 and the bacteriorhodopsin in layer of purple membrane 21. This phenomenon is known broadly as Fluorescence Resonance Energy Transfer (FRET). The relationship between distance and non-radiative transfer is given by $$R_0^6 = (8.8 \times 10^{23} \text{ mol})(\kappa^2)(\eta_D^4)(\Phi_D)(J(\lambda))) \tag{I}$$

where $R_0$ is the distance at which 50% of the donor's energy is transferred non-radiatively, K is the dipole orientation factor, $\eta_D$ is the refractive index of the medium, $\Phi_D$ is the quantum yield of the donor, and J is the normalization overlap integral between the donor and acceptor at the specific wavelength λ. Thus the efficiency, E, of the non-radiative energy transfer is indicative of R, the distance between fluorophore 28 and the bacteriorhodopsin in layer of purple membrane 21.

The efficiency of the non-radiative energy transfer is described by equation II.

$$E = \frac{R_0^6}{R_0^6 + R^6} \tag{II}$$

Because of conservation of energy, an increase in the efficiency of non-radiative energy transfer results in a consumate decrease in the efficiency of radiative energy transfer. Because bacteriorhodopsin only produces a charge gradient in the event of radiative energy transfer (i.e. fluorophore fluorescence), a decrease in distance between fluorophores 28 and the bacteriorhodopsin in layer of purple membrane 21, should result in a decreased signal measured by circuit 45.

The relationship between non-radiative energy transfer and distance produces a characteristic curve, like the one shown in FIG. 12C. (The curve in FIG. 12C is for the 565 nm emission-center quantum dot and bacteriorhodopsin system exemplified below.) As can be seen in FIG. 12C, there is an inflexion point at approximately 7.6 nm of separation between the quantum dot and the retinal molecule in the bacteriorhodopsin. Thus, at 7.6 nm of separation, small changes in distance result in dramatic changes in non-radiative transfer. Typically, sensors of the invention are engineered to have the separation between fluorophore 28 and layer of purple membrane 21 at approximately the inflexion point of the curve in the absence of targeted chemical or biological species.

Like the embodiments described above with respect to FIG. 1, the emission spectrum of fluorophores 28 may be altered by the presence of a chemical or biological species. For example, fluorophore 28 linked to layer of purple membrane 21 may undergo a conformational change in the presence of a biological species, resulting in an emission spectrum that no longer overlaps with absorption spectrum of bacteriorhodopsin 30. Alternatively, for example, the presence of a chemical species may result in a change in the electronic structure of fluorophore 28, thereby shifting emission spectrum 35 of fluorophore 28 from the peak of the bacteriorhodopsin absorption spectrum. Similar to the embodiments described with respect to FIG. 1, when a binding event causes a shift in the emission spectrum of fluorophore 28, the bacteriorhodopsin will not pump as many protons across the membrane gradient. The decrease in proton pumping diminishes the charge density at gate 41, thus the signal from circuit 45 diminishes. In other embodiments, the emission of fluorophore 28 may be quenched completely.

In embodiments where fluorophores 28 are quantum dots, it is possible to additionally functionalize the quantum dots with receptors 29 that bind targeted chemical or biological species. Receptors 29 may comprise antibodies, for example.

In the presence of shorter wavelength light 54, and in the absence of an antigen that binds to the antibody, the quantum dots emit light that overlaps the absorption spectrum of bacteriorhodopsin, producing a signal from circuit 45. When the antibody binds an antigen, however, the emission spectrum of the quantum dot shifts, resulting in a change in the signal of circuit 45.

The relationship between distance and efficiency of non-radiative transfer provides another mechanism for activating chemical/biological transistor sensor 50. Linkages 51 may be engineered such that linkages 51 have receptors for targeted chemical or biological species. In the presence of the targeted chemical or biological species, linkages 51 undergo a conformational change, thus bringing fluorophores 28 closer to layer of purple membrane 21. When fluorophores 28 move closer to layer of purple membrane 21, the amount of non-radiative energy transfer increases, resulting in a smaller charge density at gate 41, and a decreased signal from circuit 45. It is also possible that targeted chemical and/or biological binding events will result in the severance or detachment of linkages 51. The severance or detachment of linkages 51 will also result in a diminished signal from circuit 45.

Methods of using the sensors of the invention for the detection and quantification of targeted chemical or biological species are straightforward. In embodiments where the goal is merely to detect targeted chemical or biological species, it may be sufficient to merely contact the sensor with a sample, in the presence of shorter wavelength light, and observe the signal for a change. This method may be beneficial for toxin detection, for example, wherein any presence of the toxin is cause for alarm. Samples may include, but need not be limited to, bodily fluids, municipal water, air, process fluids, combustion effluent, groundwater, fuels, and foods.

In other embodiments where the goal is to quantify an amount of targeted chemical or biological species, it may be necessary to calibrate the sensor ahead of time using calibration samples having known quantities of targeted chemical or biological species. By presenting a plurality of samples with known amounts of targeted chemical or biological species and recording the signal for each calibrated sample, it is possible to construct a correlation that can be used to quantify an amount of targeted chemical or biological species in a sample. For example, five calibration samples may be presented to the sensor, resulting in five different signals. The signals of the five calibration samples may be correlated to known amounts of targeted chemical or biological species using a least-squares fitting function. The correlation resulting from the least-squares fitting function can be used to quantify amounts of targeted chemical or biological species in samples based upon the signal. Other methods of correlating signal to amount are known to those of skill in the art.

EXAMPLES

The following non-limiting examples further illustrate the sensors of the invention.

Example 1

Preparation of Oriented Purple Membrane

The process of preparing and purifying bacteriorhodopsin for engineered applications has been described (Stuart, Preparation, purification and modification of bacteriorhodopsin for use in protein-based optical devices). In brief, the *Halobacterium salinarium* cells were grown at 40° C. in a basal salts medium containing bacteriological peptone. Once grown to a desired density, the cells were collected by centrifugation at 17,700 g for 10 minutes. The collected cells were then lysed through the addition of deionized water. The released nucleic acids were digested with 1-3 Units/ml, final solution volume, of DNase I. The larger cell debris was collected through centrifugation at 3,000 g for 5 minutes. Purple membrane (bacteriorhodopsin and associated lipids) remained in the supernatant and was separated from the red membrane by centrifugation at 105,000 g for 30 minutes. The purple membrane was pelleted in this centrifugation step, which was repeated until the supernatant was clear. For additional purification, the purple membrane was passed over a linear sucrose gradient. The purity of the resulting bacteriorhodopsin preparation was evaluated by sodium dodecyl sulfate-polyacrylamide gel electrophoresis (SDS-PAGE) on a 12% Bis-Tris gel.

Figure 6:
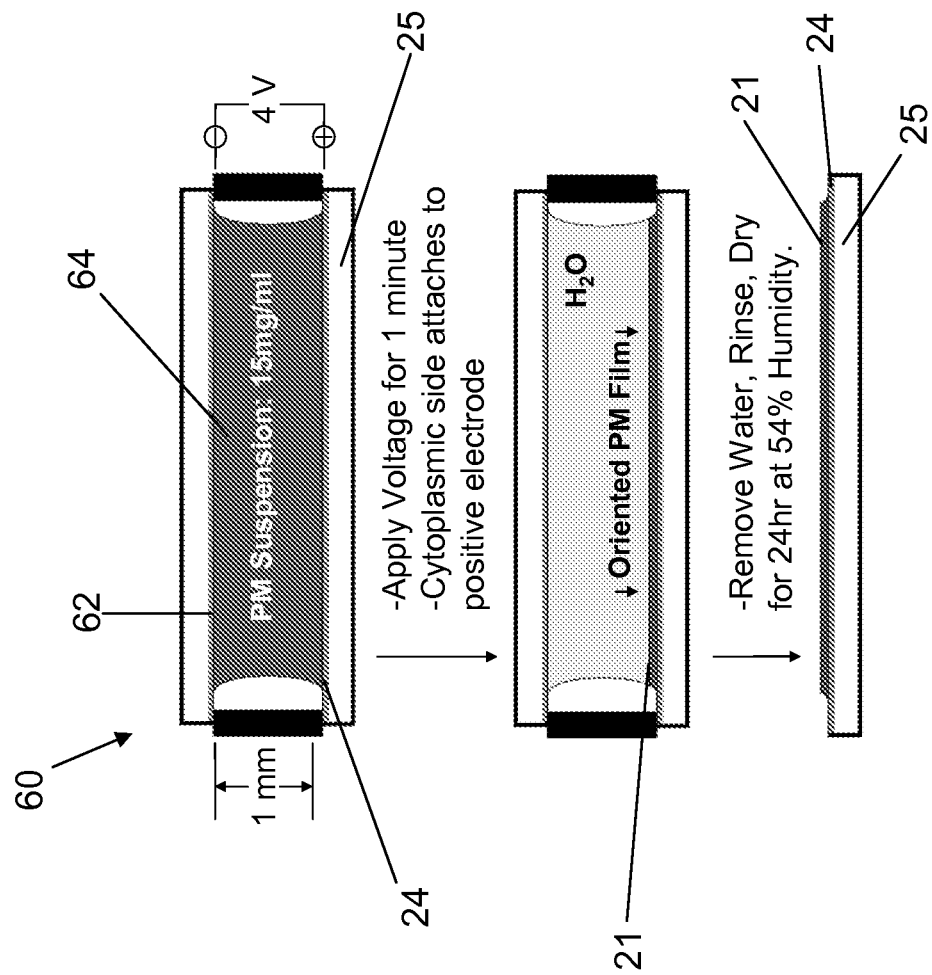
FIG. 6 is a schematic diagram of the protocol for producing oriented purple membrane (PM) films.

Purple membrane layer for a sensor was created using electrophoretic sedimentation (EPS) as shown in FIG. 6. This method provides a layer of purple membrane comprising highly-orientated bacteriorhodopsin, e.g., the cytoplasmic ends of the bacteriorhodopsin are identically-oriented. A fixture 60 was constructed to hold substrate 25 (glass slide) with first electrode 24, and a brass electrode 62 apart, with a separation distance of approximately 1 mm. The distance of separation is not critical, and the EPS will work with larger and smaller separations. First electrode 24 (positive electrode) is a sputtered layer of optically transparent and electrically conductive indium tin oxide (ITO) on substrate 25. The dimensions of the slide (25) were 5 mm×10 mm and electrode 24 had a sheet resistance of 5-10Ω. Thirty μl of suspension 64 of 15 mg/ml purple membrane in distilled/deionized water (ddI) water was pipetted on top of first electrode 24 and substrate 25. The brass electrode 62 (negative electrode) was placed on top with 1 mm spacing between the electrodes. An electric field of 40 V/cm was applied between the electrodes for 1 minute, as depicted in FIG. 6. It was possible to visually observe layer of purple membrane 21 deposit out of suspension 64 and attach to first electrode 24 while the electric field was being applied.

Following the 1 minute exposure to the electric field, the top brass electrode 62 was removed and the excess water was pipetted off layer of purple membrane 21. First electrode 24 with attached layer of purple membrane 21 was then rinsed for 10 seconds in a beaker of distilled/deionized water to remove any weakly attached purple membrane. First electrode 24 with attached layer of purple membrane 21 was then stored in a humidity chamber for 24 hours to dry. Humidity in the chamber was maintained at ~52% through the use of a magnesium nitrate salt solution. The dimensions of substrate 25 with attached first electrode 24 with attached layer of purple membrane 21 was approximately 5 mm×5 mm with a thickness of layer of purple membrane 21 of approximately 20 μm measured with an interferometric microscope.

Figure 7:
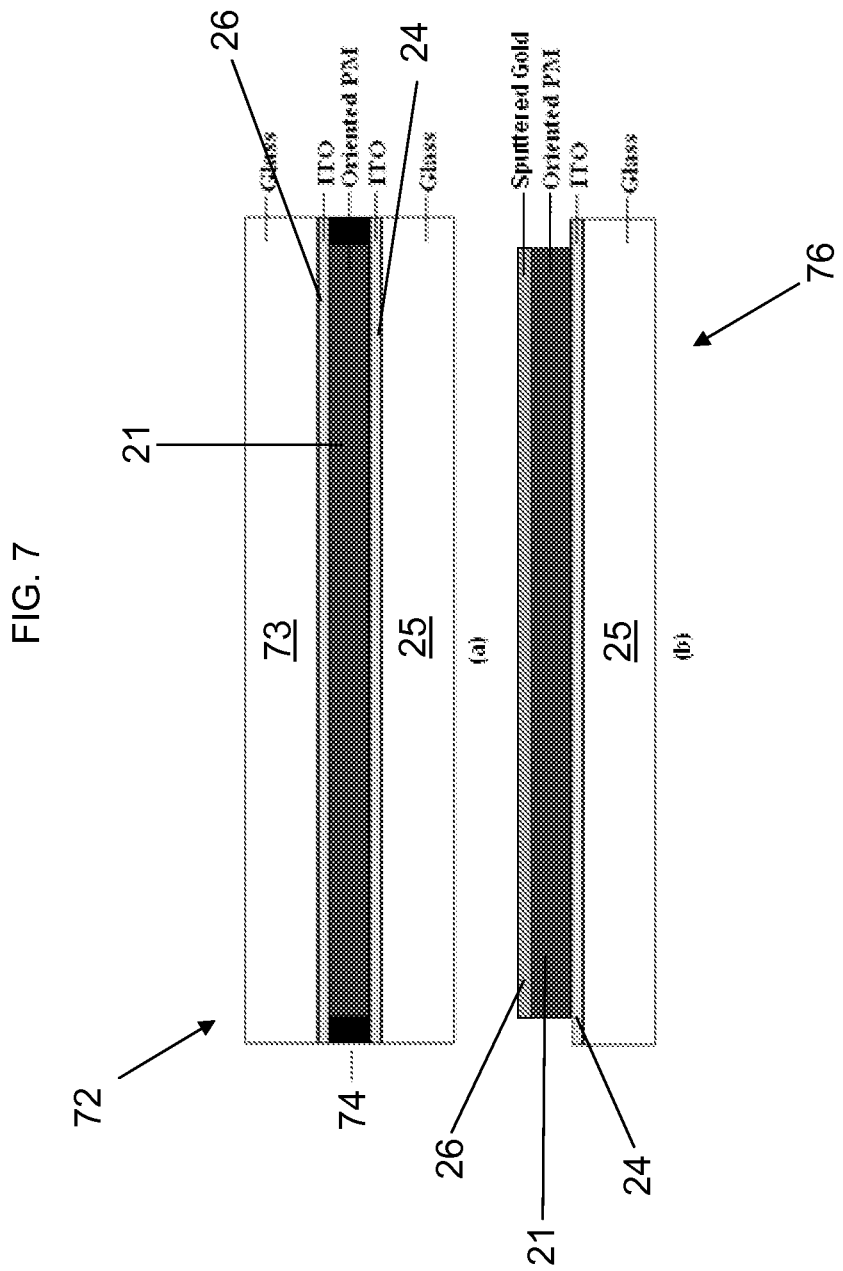
FIG. 7 is schematic diagram of completed wet (a) and dry (b) PM film assemblies.

For applications which require a wet layer (aqueous suspension) of layer of purple membrane 21, a glass slide 73 with second electrode 26 (also indium-tin-oxide) may be placed atop a prior assembly of substrate 25, electrode 24, and layer of purple membrane 21 after rinsing (above) but before drying (above), as shown in FIG. 7 (a). In order to maintain the aqueous environment, it is necessary to add a spacer 74 around the perimeter of the layer of layer of purple membrane 21 in order to keep layer of purple membrane 21 wet. Spacer 74 may be, for example, a rubber O-ring. The resulting construct is hereafter a wet assembly 72.

Alternatively, some applications require dry layer of purple membrane 21. For these applications, substrate 25 with attached first electrode 24 with attached layer of purple membrane 21 can be dried as described above and shown in FIG. 6, and the resulting layer of purple membrane 21 sputtered with a layer of gold to create second electrode 26, to create the structure shown in FIG. 7 (b). The resulting construct is hereafter a dry assembly 76.

Figure 8:
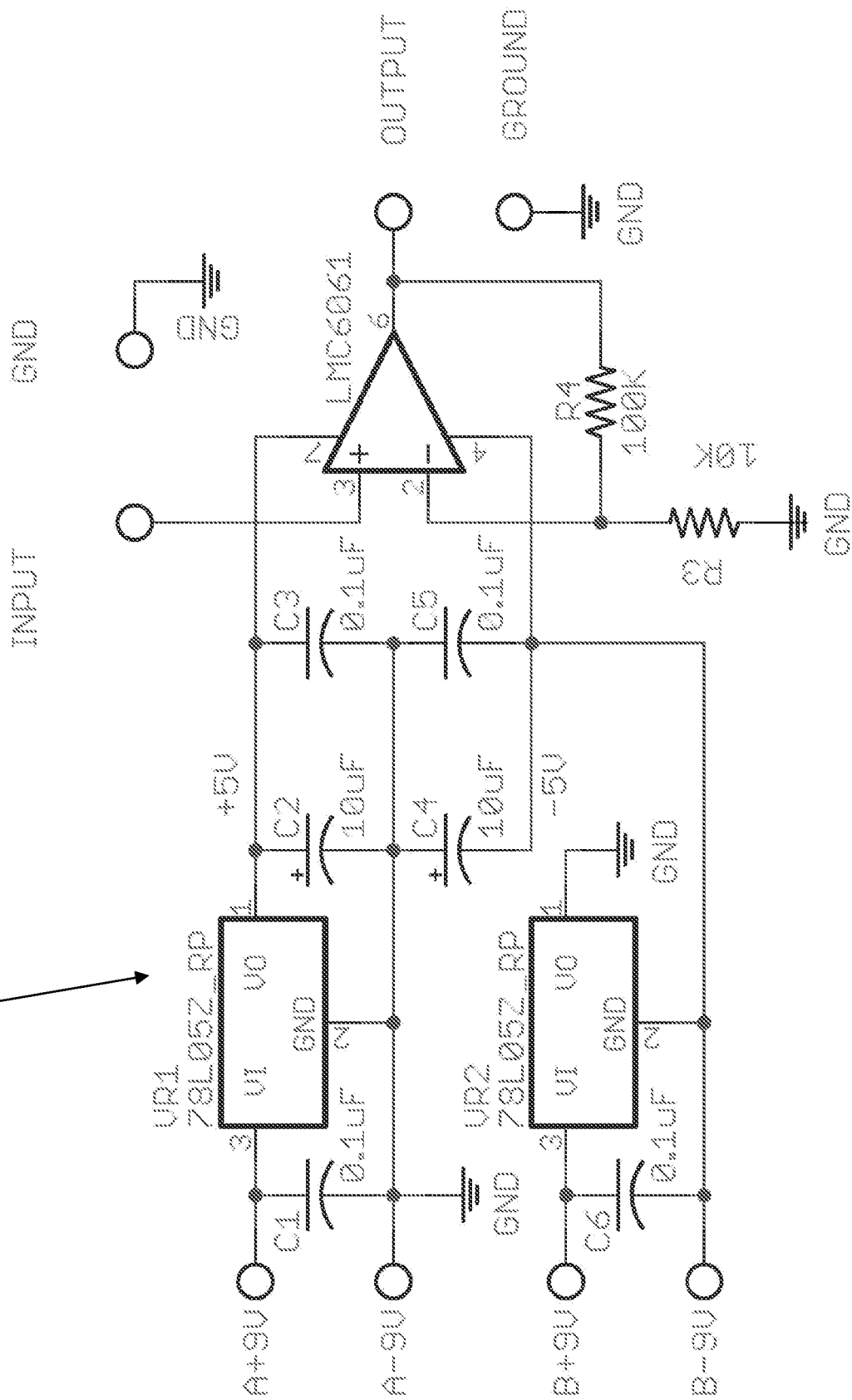
FIG. 8 is a diagram of an electronic circuit used to measure charge gradients.

A representative circuit 30 capable of producing a signal in response to a charge gradient across layer of purple membrane 21 is shown in FIG. 8. Circuit 30 can measure a change in voltage (ΔV) between first electrode 24 and second electrode 26 in either wet assembly 72 or dry assembly, and amplify the ΔV for recording by an oscilloscope or computer. Circuit 30 comprises an operational amplifier, resistors, and capacitors as necessary to reduce noise and achieve the desired amplification of the ΔV between first electrode 24 and second electrode 26. Electronic circuit 30 shown in FIG. 8 acts as a ×10 amplifier, however other amplifications are possible and the modifications necessary to achieve alternate amplifications are known to those of skill in the art. For the experiments shown herein, bacteriorhodopsin-based sensor 20 and circuit 30 were placed inside a Faraday cage to reduce RF noise. Circuit 30 was powered by a triple output voltage supply (HP 6237A, Agilent Technologies, Santa Clara, Calif.). The output signal from circuit 30, $V_{out}$, was run through a low-frequency noise filter (Krohn-Hite 3364, Krohn-Hite, Brockton, Mass.). After filtering, the conditioned signal is sent into a 60 MHz, 200 MSa/s oscilloscope (Agilent 54621D, Agilent Technologies, Santa Clara, Calif.) for analysis.

Example 2

Addition of Quantum Dot Layer to Wet Assembly

Quantum dots (Evident Technologies, Troy, N.Y.) having an emission band centered at 565 nm were chosen to maximize the overlap between quantum dot fluorescence spectrum 35 and bacteriorhodopsin absorption spectrum 30. This overlap is depicted in FIG. 3.

Figure 9:
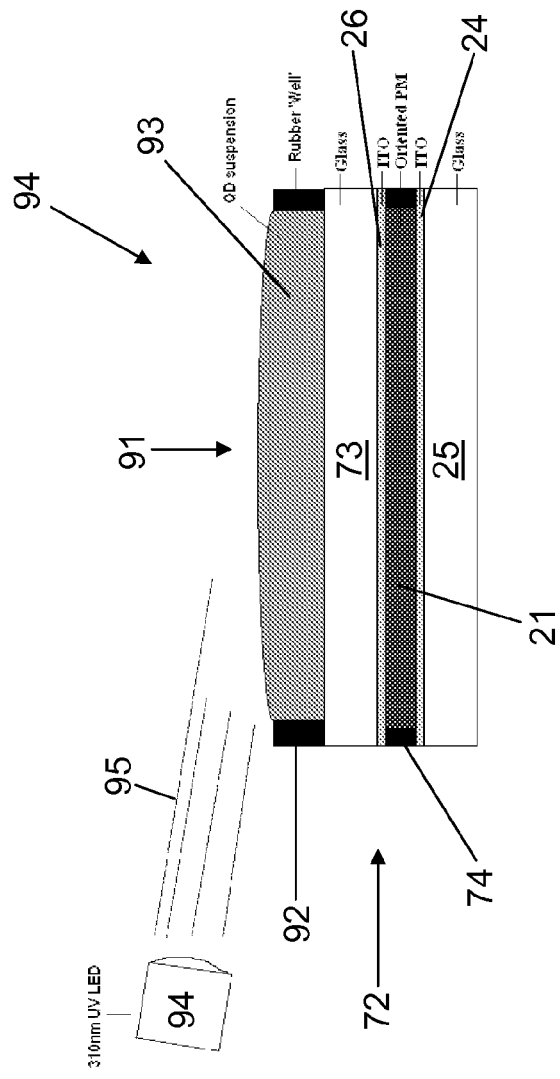
FIG. 9 shows a wet quantum dot-bacteriorhodopsin light sensor, and a signal from a wet quantum dot-bacteriorhodopsin light sensor.
Figure 9:
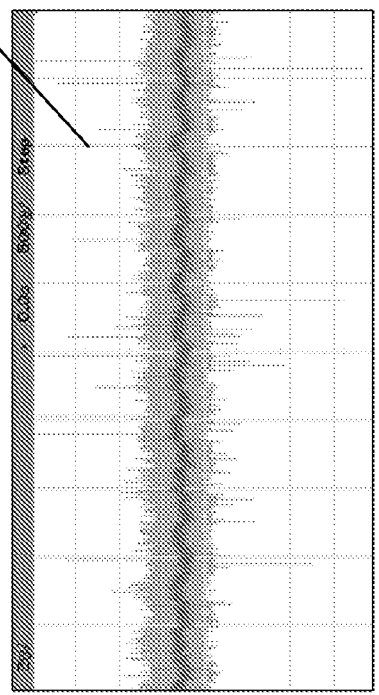

FIG. 9A shows a completed quantum dot, bacteriorhodopsin-based optical sensor 90 with circuit 30 removed. A well 91 was formed by placing a rubber gasket 92 around the perimeter of the back side of glass slide 73 of wet assembly 72. A 40 μL volume of 63 nmol/L quantum dot suspension 93 was applied added to well 91. A 310 nm light-emitting diode (LED) 94 was arranged at an angle so that LED 94 would illuminate the layer of quantum dots with UV light 95, with minimal direct exposure of the bacteriorhodopsin in layer of purple membrane 21. With LED 94 flashing at approximately 4 Hz, the quantum dots were visibly activated, and their photonic emission resulted in a ΔV and corresponding peaks 99, as shown in FIG. 9B. The periodic peaks 99 generated from bacteriorhodopsin-based optical sensor 90 directly correlated to the flashing of the LED 94.

Example 3

Addition of Quantum Dot Layer to Dry Assembly

Dry assembly 76 was prepared as described above. A 63 nmol/L suspension of quantum dots was pipetted upon the second electrode 26, and the quantum dot suspension is allowed to dry. A semiconductor parameter analyzer was used in lieu of the low-frequency noise filter and oscilloscope in order to increase sensitivity.

Figure 10:
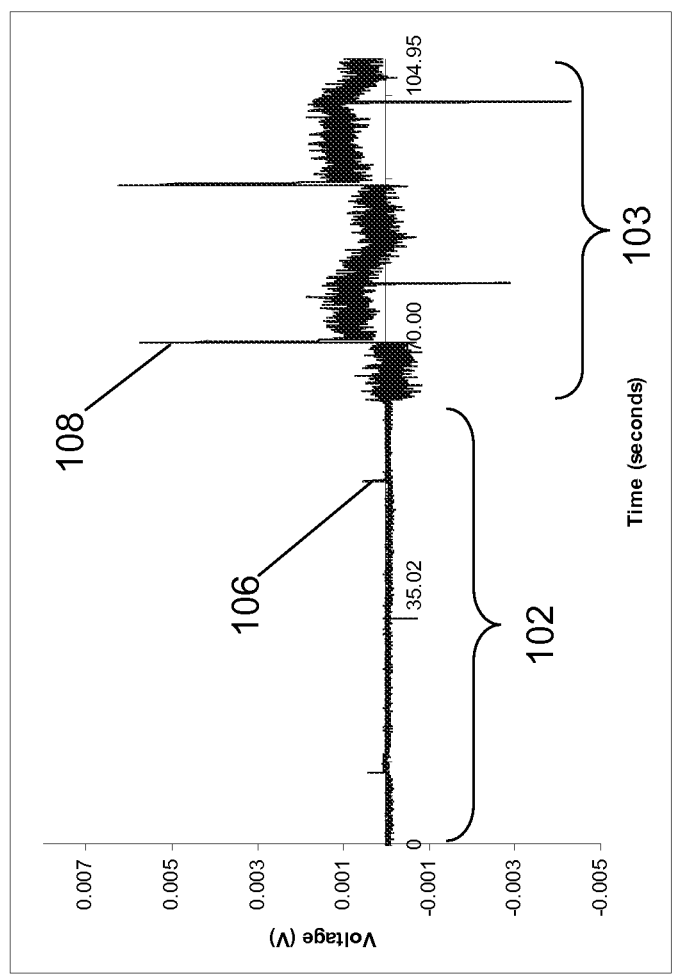
FIG. 10 is a signal from a dry quantum dot-bacteriorhodopsin light sensor.

Dry assembly 76 with quantum dots, and without quantum dots, were compared to judge the signal boost gained from the addition of the quantum dots. As in previous examples, the sensors were exposed to flashing LEDs. FIG. 10 shows a comparison of the UV-light sensitivity of dry assembly 76 before 102, and after 103, the deposition of the quantum dots. As can be seen from FIG. 10, there are some small peaks 106 attributable to the flashing LED before 102 the quantum dots are deposited. However, the signal peaks 108 increased nearly an order of magnitude once the quantum dots were deposited.

Comparing the signals of "wet" bacteriorhodopsin-based optical sensor 90 (FIGS. 9A, B) to "dry" bacteriorhodopsin-based optical sensor (FIG. 10), it is clear that the wet sensor has a much larger signal output than the dry sensor for similar UV-illumination events. This is not surprising, given the difference in the spacing between layer of purple membrane 21 and the quantum dot layers in the wet and dry sensors, respectively. As seen in FIG. 12A, the spacing between layer of purple membrane 21 and quantum dots in the "wet" sensor is approximately 1 mm, corresponding to the thickness of glass slide 73. As seen in FIG. 12B, the spacing between layer of purple membrane 21 and quantum dots in the dry sensor is approximately 4 nm, the thickness of second electrode 26. Again, because of the relationship between distance and non-radiative transfer, illustrated in FIG. 12C, it is expected that signal due to radiative energy transfer would be smaller in the "dry" sensor where the quantum dots and the bacteriorhodopsin are close together.

Example 4

Preparation of Thin Oriented Purple Membrane

The fabrication methods described in Example 1 produce oriented purple membranes on the order of 20 μm thick. However, in order to take advantage of changes in radiative versus non-radiative energy transfer, it is necessary to produce oriented purple membranes on the order of tens of nanometers thick, preferably one monolayer of purple membrane (e.g., comprising only bacteriorhodopsin and a singular lipid bilayer). As in Example 1, *Halobacterium salinarium* cells were grown at 40° C. in a basal salts medium containing bacteriological peptone. Once grown to a desired density, the cells were collected by centrifugation at 17,700 g for 10 minutes. The collected cells were then lysed through the addition of deionized water. The released nucleic acids were digested with 1-3 Units/ml, final solution volume, of DNase I. The larger cell debris was collected through centrifugation at 3,000 g for 5 minutes. Purple membrane (bacteriorhodopsin and associated lipids) remained in the supernatant and was separated from the red membrane by centrifugation at 105,000 g for 30 minutes. The purple membrane was pelleted in this centrifugation step, which was repeated until the supernatant was clear. For additional purification, the purple membrane was passed over a linear sucrose gradient. The purple membrane was then suspending in distilled deionized water.

An electrode of indium tin oxide was deposited on a substrate. The substrate with electrode was coated with poly (dimethyldiallylammonium) chloride using a Langmuir-Blodgett trough, to produce a surface-charged electrode-substrate assembly. When the surface-charged electrode-substrate assembly was soaked in a purple membrane suspension for approximately 5 minutes, a monolayer of oriented purple membrane was deposited upon the electrode. When allowed to dry under controlled humidity, the resultant monolayer of oriented purple membrane was quite robust.

Example 5

Thin Oriented Purple Membrane—Quantum Dot Light Sensor

Using the techniques described in Example 4, a monolayer of oriented purple membrane was deposited upon an indium tin oxide (ITO) electrode atop a substrate. In an iterative fashion, a layer of poly(dimethyldiallylammonium) was deposited upon the first monolayer of purple membrane, then a second layer of purple membrane was deposited upon the layer of poly(dimethyldiallylammonium), then a layer of poly(dimethyldiallylammonium) was deposited upon the second monolayer of purple membrane, then a third layer of purple membrane was deposited upon the layer of poly(dimethyldiallylammonium). The third monolayer of purple membrane was biotinylated prior to deposition by mixing biotin into a suspension of purple membrane fragments in 0.1 M sodium bicarbonate buffer (pH of about 8.5). After the purple membrane monolayers were deposited, a platinum wire was placed in proximity to the purple membrane monolayers, and two drops of 0.1 M KCl were added to assure electrical contact. The ITO electrode and platinum wire were then attached to a ×10 preamp and oscilloscope. When a Xenon lamp was switched on, a peak was visible on the oscilloscope, which decayed away in approximately 2 seconds. When the Xenon lamp was switched off, a negative peak was visible. See FIG. 11, "no QD."

Figure 11:
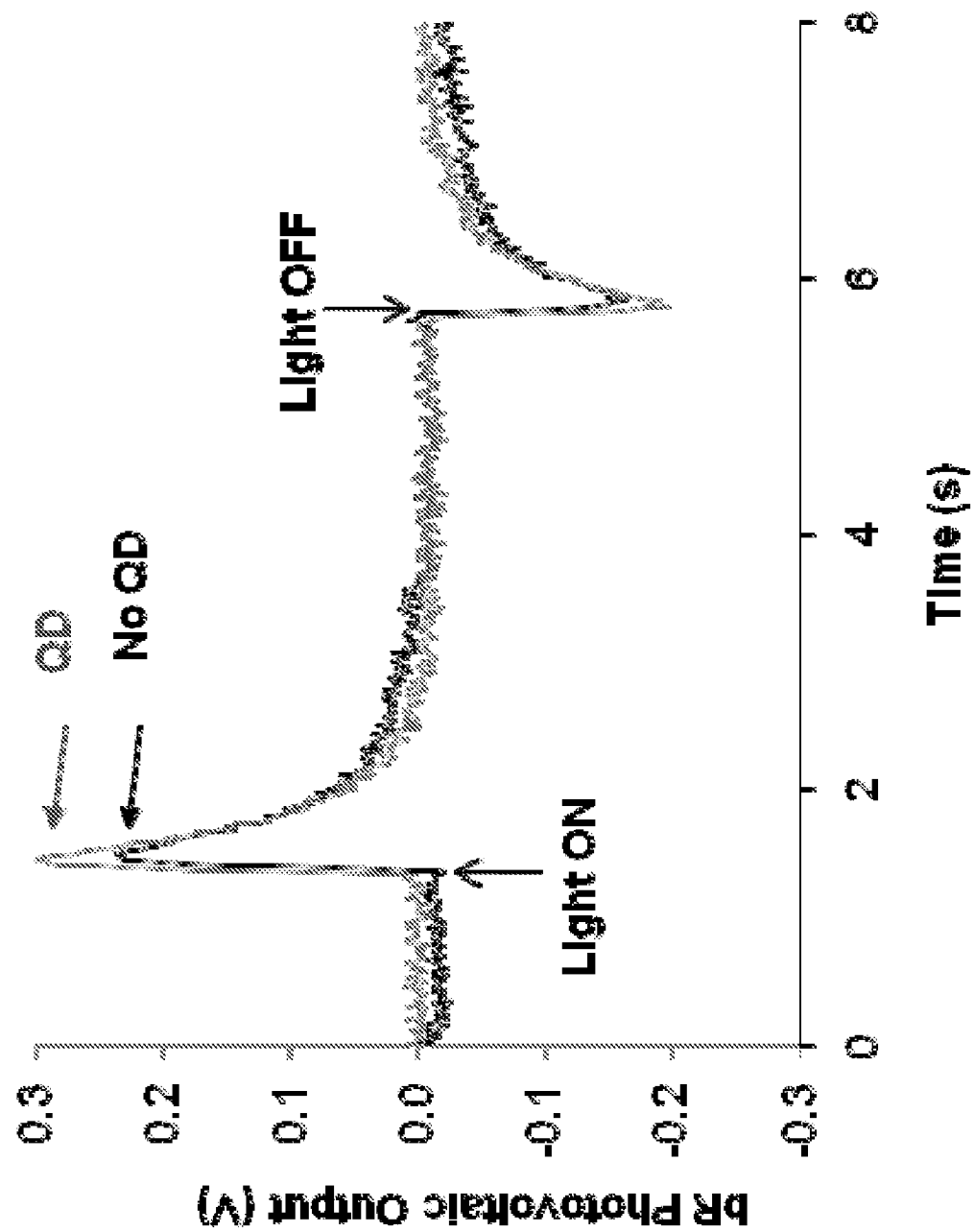
FIG. 11 compares a signal from a three monolayer bacteriorhodopsin light sensor to a signal from a three monolayer bacteriorhodopsin light sensor with attached quantum dots.

The platinum wire was then removed, the KCl pipetted away, and the purple membrane layers washed with Dl water. The assembly was then incubated with 0.5 nmol/ml streptavidin-coated quantum dots (595 nm emission center) for 15 minutes. After the incubation period the assembly was rinsed for 2 minutes in Dl water to remove any unbound quantum dots. The platinum wire was replaced, two drops of KCl solution were added, and the sensor reattached to the preamp and oscilloscope. As can be seen in FIG. 11 the resulting sensor had a similar response to the Xenon light, however the amplitude of the response was greater. See FIG. 11, "QD." The response was greater because the quantum dots allowed the bacteriorhodopsin in the purple membrane to use a greater number of the photons emitted from Xenon light spectrum. That is, some of the photons that were too energetic to be captured by the bacteriorhodopsin were transferred to the bacteriorhodopsin via the quantum dots.

Prophetic Examples

Example 6

Maltose Sensor

Figure 13:
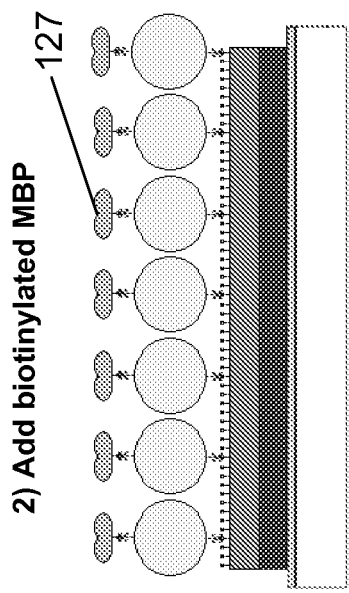
FIG. 13 is a schematic diagram of the protocol for the construction of a maltose sensor.
Figure 13:
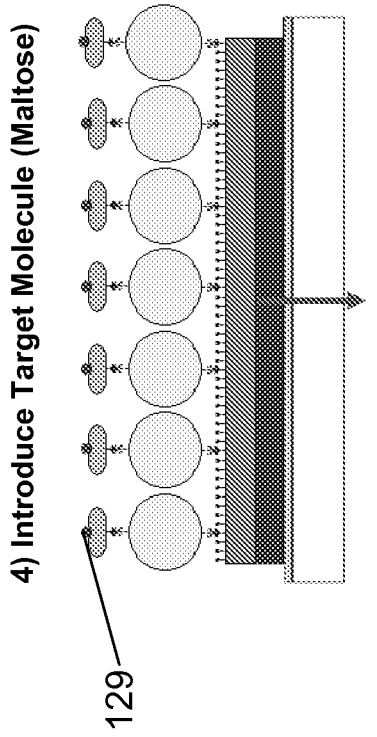
Figure 13:
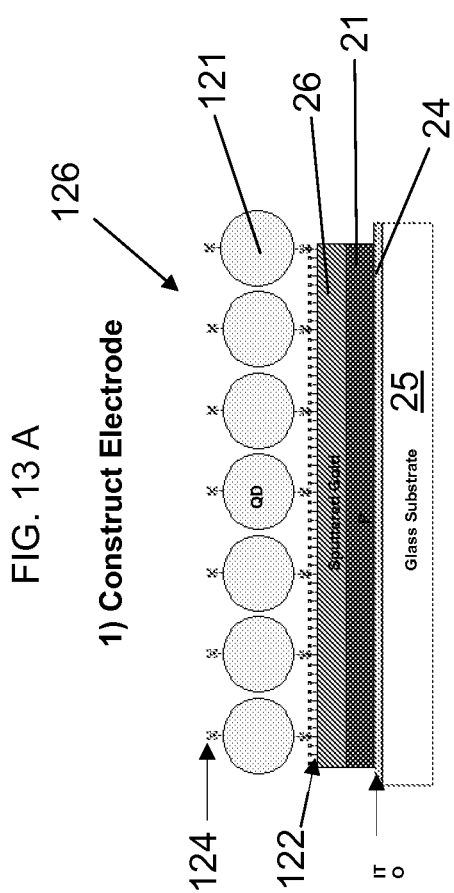
Figure 13:
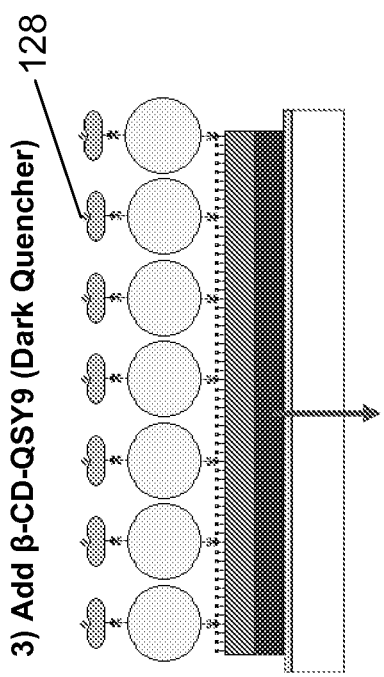

A maltose sensor according to the invention is depicted in FIG. 13. The maltose sensor will begin with a dry assembly such as that described in Example 1. Using biotin-streptavidin linkages, a layer of quantum dots 121 will be added to the gold electrode of dry assembly 76. The distance R, between the quantum dots 128 and layer of purple membrane 21 will be selectively fixed at approximately 8 nm by linking quantum dots 121 directly to second electrode 26, as seen in FIG. 13A. An 8 nm separation between quantum dots 121 and layer of purple membrane 21 will result in the greatest sensitivity of the sensor to changes in distance due to binding of chemical species.

As shown in FIG. 13A, the dry sensor will be prepared with a second electrode 26 of sputtered gold. The sputtered gold surface will be biotinylated with biotin 122 using known techniques. Quantum dots 121 will be coated with a single monolayer of streptavidin 124. When biotinylated second electrode 26 is exposed to streptavidin-coated quantum dots 121, the quantum dots will self-assemble at a distance approximately 8 nm from layer of purple membrane 21. The quantum dot-linked dry assembly 126 will then be washed with distilled deionized water to remove the excess quantum dots 121.

As shown in FIG. 9B-D, quantum dot-linked dry assembly 126 becomes the basis for a maltose sensor. Quantum dot-linked dry assembly 126 will be washed with biotin coated maltose-binding protein 127 (FIG. 13B). The assembly shown in FIG. 13B will give a consistent signal upon illumination with UV-light, as shown previously in FIGS. 9B and 10, because the distance between quantum dots 121 and layer of purple membrane 21 is approximately 8 nm. However, when a β-CD-QSY9 dark quencher 128 is introduced to maltose binding protein 127, dark quencher 128 occupies the binding site that would otherwise be taken by maltose. (See FIG. 13C.) Because dark quencher 128 essentially short-circuits the radiative energy transfer pathway, there is no signal from the sensor. Upon introduction of maltose 129, dark quencher 128 is displaced, re-establishing the radiative energy transfer pathway for quantum dots 121, as shown in FIG. 13D. Once the radiative energy transfer pathway is re-established, a signal will be produced by the sensor. Thus, the sensor in FIG. 13 is silent until maltose is present, at which point the sensor produces a signal.

Example 7

Antibody Sensor

Figure 14:
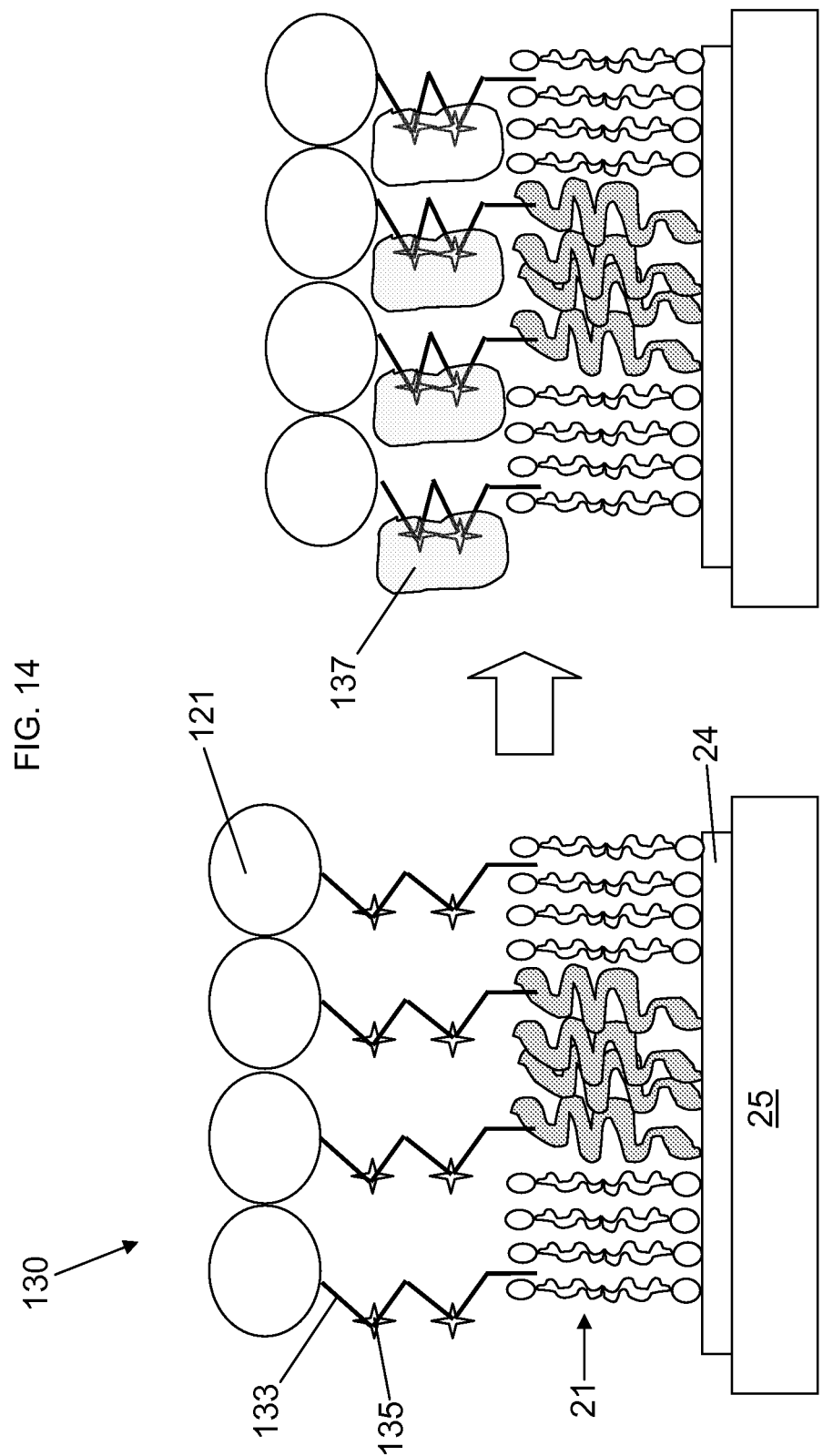
FIG. 14 is a schematic diagram of an antibody sensor according to the invention.

An antibody sensor according to the invention is described in FIG. 14. Instead of functionalizing quantum dots 121 as in FIG. 13, linkages 133 are functionalized with antigens 135 specific to antibodies 137 of interest. Absent antibody 137, quantum dots 121 are maintained 8 nm from layer of purple membrane 21 because of linkages 133. Again, as shown in FIG. 12C, when quantum dots 121 and layer of purple membrane 21 are separated by more than 8 nm, there is little non-radiative transfer. Thus, circuit 30 (not shown) produces large signals in the absence of non-radiative transfer. However, when antibody 137 is introduced, antibody 137 will cause a conformational change in linkage 133, bringing quantum dots 121 closer to layer of purple membrane 21. As quantum dots 121 move closer to layer of purple membrane 21, the amount of non-radiative transfer increases, and therefore, the signal decreases. Thus, the sensor in FIG. 14 will produce a signal until the introduction of antibody 137, at which time the signal will decrease.

Example 8

Chemical Sensor Array

Figure 15:
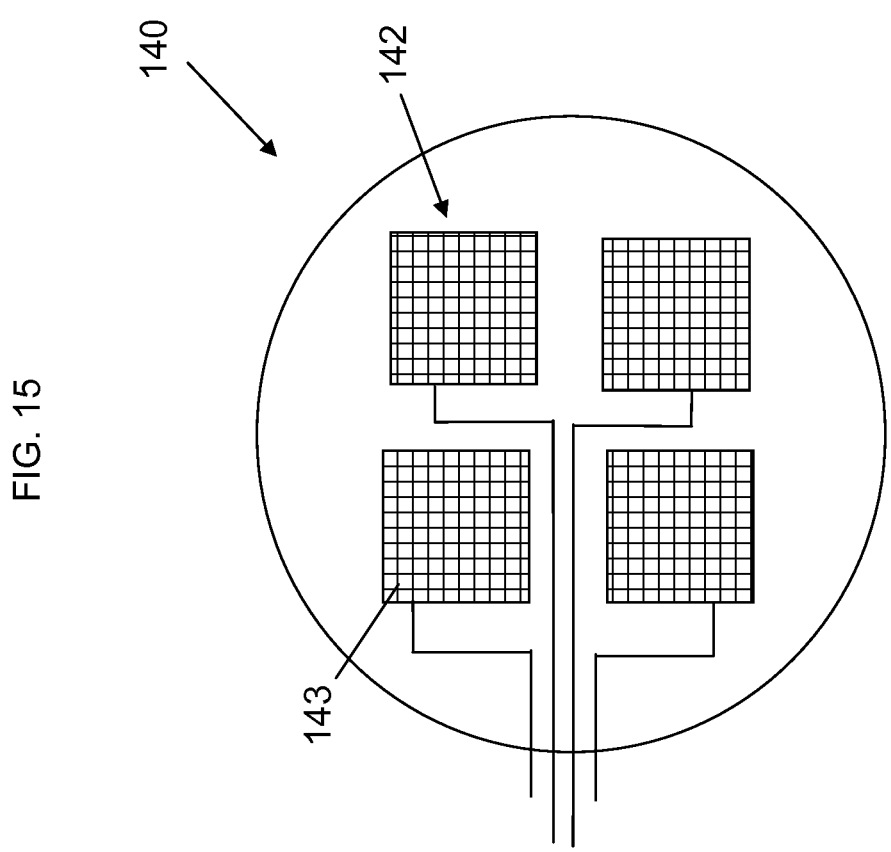
FIG. 15 is a depiction of an array of sensors according to the invention.

A chemical sensor array 140 will be constructed from a field of FETs prepared on a silicon chip using known semiconductor fabrication techniques. Chemical sensor array 140 is depicted in FIG. 15. Chemical sensor array 140 will have four groups 142 of 144 FETs. (Each FET 143 is a separate source, drain, gate, body arrangement as shown in FIGS. 4 & 5.) Using iterative photolithographic techniques, the gates of the FETs 143 in each of the four separate groups 142 will be exposed and activated, so that the gates in that region will receive one or more monolayers of oriented purple membrane. A solution of quantum dots with functionalize linkages will then be introduced to the sensor, resulting in 144 FET sensors similar to those described in FIG. 5 and FIG. 14. After the first group of 144 FETs has been transformed into chemical sensors, the second group of FETs will be transformed. However, this group will have functionalized linkages that are specific to a different chemical target. In an iterative fashion, the third and fourth FET groups are converted to chemical sensors. The finished chemical sensor array 140 will have 576 total chemical sensors. The finished chemical sensor array 140 will be sensitive to four different chemical species.

Thus, the invention provides, among other things, a bacteriorhodopsin-based sensor capable of detecting chemical and or biological species. Various features and advantages of the invention are set forth in the following claims.

We claim:

1. A sensor comprising:
a substrate;
a first electrode in contact with the substrate;
a membrane adjacent to the first electrode, wherein the membrane comprises bacteriorhodopsin;
a second electrode adjacent to the membrane, wherein charge is transferred between the first and second electrodes when the membrane is exposed to visible light; and
a circuit operatively connected to the first and second electrodes, wherein the circuit produces a signal when charge is transferred between the first and second electrodes;
wherein the sensor comprises a fluorophore adjacent to the second electrode and the fluorophore transfers energy to the membrane when the fluorophore is exposed to light with a wavelength shorter than 570 nm.

2. The sensor of claim 1, wherein the membrane is purple membrane.

3. The sensor of claim 2, wherein the purple membrane is wet.

4. The sensor of claim 2, wherein the purple membrane is dry.

5. The sensor of claim 1, wherein the fluorophore is attached to the membrane with a linker molecule.

6. The sensor of claim 5, wherein the linker molecule is a biotin-streptavidin construct.

7. The sensor of claim 1, wherein the energy transfer between the fluorophore and the membrane comprises a radiative process.

8. The sensor of claim 1, wherein the energy transfer between the fluorophore and the membrane comprises a non-radiative process.

9. The sensor of claim 1, wherein the fluorophore is a quantum dot.

10. The sensor of claim 9, wherein the quantum dot is functionalized.

11. The sensor of claim 10, wherein the functionalized quantum dots are functionalized with receptors that bind targeted chemical or biological species.

* * * * *